United States Patent [19]

Engelhardt et al.

[11] Patent Number: 4,805,607
[45] Date of Patent: Feb. 21, 1989

[54] MODULAR INTRAMEDULLARY NAIL SYSTEM

[75] Inventors: John A. Engelhardt; Richard R. Tarr, both of Warsaw, Ind.

[73] Assignee: Boehringer Mannheim Corporation, Indianapolis, Ind.

[21] Appl. No.: 128,091

[22] Filed: Dec. 3, 1987

[51] Int. Cl.⁴ ............................................. A61F 5/04
[52] U.S. Cl. ........................... 128/92 YZ; 128/92 YY
[58] Field of Search .......... 128/92 Y, 92 YY, 92 YK, 128/92 YS, 92 YZ; 623/22

[56] References Cited

U.S. PATENT DOCUMENTS

| | | | |
|---|---|---|---|
| 1,043,027 | 10/1912 | Newman | 24/150 P |
| 2,222,517 | 11/1940 | Price | 128/92 YK |
| 2,239,088 | 4/1941 | Ettinger | 128/92 YK |
| 3,181,189 | 5/1965 | Leyden | 15/22 R |
| 3,390,589 | 6/1968 | Tschanz | 24/625 |
| 3,530,854 | 9/1970 | Kearney | 128/92 YK |
| 4,012,155 | 3/1977 | Morris | 24/625 |
| 4,438,762 | 3/1984 | Kyle | 128/92 YK |
| 4,467,794 | 8/1984 | Maffel | 128/92 R |
| 4,530,355 | 7/1985 | Griggs | 128/92 R |
| 4,622,959 | 11/1986 | Marcus | 128/92 YZ |
| 4,640,271 | 2/1987 | Lower | 128/92 YF |
| 4,705,027 | 11/1987 | Klaue | 128/92 YY |

Primary Examiner—Robert A. Hafer
Assistant Examiner—Kevin G. Rooney
Attorney, Agent, or Firm—Perman & Green

[57] ABSTRACT

A modular intramedullary nail system for the repair of long bone fractures. The system comprises several base nails of different lengths and diameters, each of which may be anatomically curved, and several extension members of different lengths and diameters. By selection of various combinations of base nails and extension members, nails of substantially any length and diameter can be constructed at the time of surgery. Nails for left and right bones are interchangeable. A unique construction enables an extension member to be readily and fixedly joined to the trailing end of a base nail so as to prevent inadvertent separation of the base nail and extension member while maximizing strength of the modular nail. The base nail is preferably tri-flanged, each flange terminating at a sharp point at its distal end. Cross screws may also be employed to prevent relative motion between the bone and the nail and also serve to prevent unlocking of the extension member from the base nail.

21 Claims, 2 Drawing Sheets

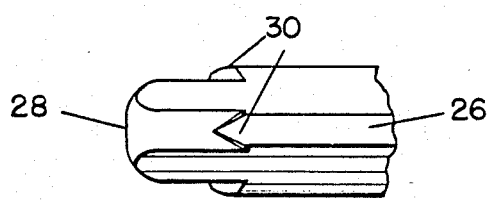
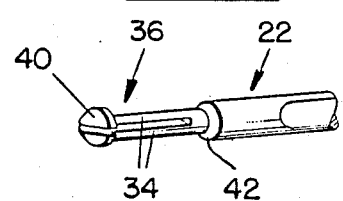
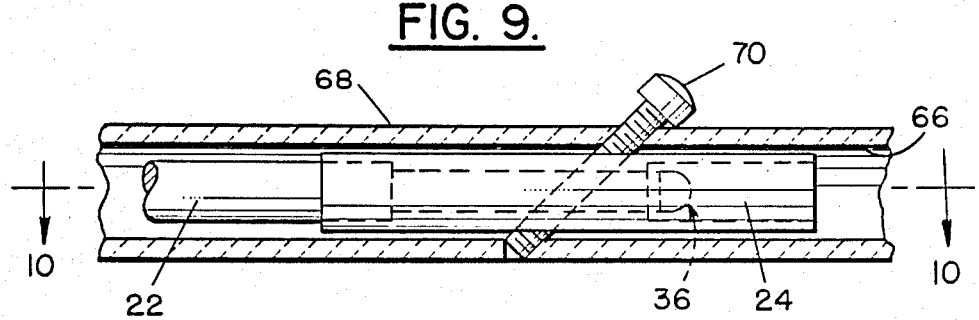
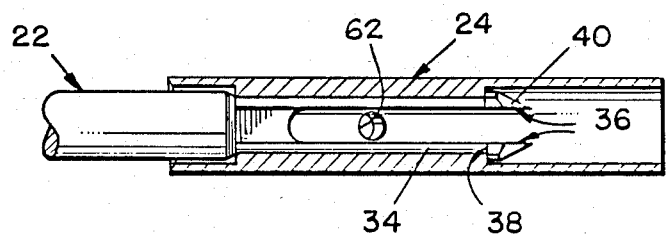
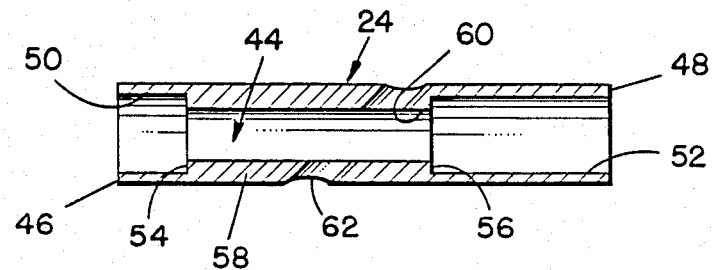

MODULAR INTRAMEDULLARY NAIL SYSTEM

BACKGROUND OF THE INVENTION

I. Field of the Invention

The present invention relates to a modular intramedullary nail system for the repair of long bone fractures which provides for a large number of resulting nail sizes from a relatively small number of base nails and extension members.

II. Description of the Prior Art

The concept of using various fastening devices for rejoining bones which have become fractured is well known. For example, U.S. Pat. No. 4,467,794 discloses an assembly which comprises a pair of tubular members adapted to be inserted in the intramedullary passages of the respective parts of a broken bone. U.S. Pat. No. 3,530,854 discloses a telescoping nail assembly which is of particular value in repairing fractures in the femoral head. Similar bone screw devices are also disclosed in U.S. Pat. Nos. 4,530,355, and 4,640,271.

It is noteworthy, however, that in none of the prior patents just cited, is there provision of any structure which prevents relative movement, either rotationally or longitudinally, between the components of the fastener system.

Although the foregoing devices satisfy the goals for which they each intended, none specifically addressed the problem of providing a modular intramedullary nail system by reason of which a relatively small number of inventoried components would satisfy virtually all requirements within a hospital setting. It was with knowledge of the prior art and of the situation then existing that the present invention has been conceived and reduced to practice.

SUMMARY OF THE INVENTION

The invention comprises a base nail generally conforming to the shape of the bone and an extension member which is snapped onto the trailing end of the base nail. It is intended that the system be sold as a set of several base nails of different lengths and diameters and several snap on extension members of different lengths and diameters. The components can be selected by the surgeon and assembled in the operating room to thereby achieve an intramedullary nail of the desired size and, also, left and right orientation.

The number of nails to be stocked in hospital inventory to ensure proper sizing is a major problem. Since intramedullary nailing is used for cases of traumatic injury, an adequate stock must be kept on hand to provide prompt availability for all possible patients. Typical femoral intramedullary nail sets, for example, range from 12 to 18 mm diameters in 1 mm increments and lengths from 32 to 48 cm in 2 cm increments. For sets with separate nails for left and right femurs, the number of components representing a full set can be as high as 84 pieces. A modular system by which any length nail could be constructed in the operating room would clearly be of immense advantage.

The modular system of the invention comprises several base nails of different lengths and diameters and several extension members of different lengths and diameters. By selection of various combinations of base nails and extension members, nails of substantially any length can be constructed at the time of surgery. Furthermore, by turning the extension 180°, a left nail becomes a right and vice versa. An added advantage to this system is that once a nail is installed, the surgeon may adjust the length of the nail and/or the targeting of a cross screw by removing and replacing the extension member while leaving the base nail in position.

One of the main concerns of intramedullary nailing is the fact that most systems in current use require reaming to insure proper fit and ease of installation. As a result of the reaming of the intramedullary canal, however, severe compromise of endosteal tissue can occur. This may result in tissue necrosis due to heat or vascular disruption. The invention offers the surgeon the option of not reaming the canal as a preparation for installation of the nail. The tri-flanged nail design allows cortical contact along three very thin flanges of metal that are equally spaced. At the leading end of each flange is a sharp point that upon nail impaction cuts into the cortex and provides a self broaching mechanism. Between contact areas of the nail are large sections around which endosteal tissue is not compromised providing channels for revascularization. The localized nature of cortical contact in the tri-flanged design provides superior rotational stability of the nail in both the interlocked and non-interlocked mode.

Other femoral nails commercially available at present are generally curved to a radius in excess of 100 inches. It can be shown that the radius of curvature of the human femur is actually on the order of approximately 60 to 80 inches. The system of the invention, therefore, utilizes base nails having a radius generally in the range of 60 to 80 inches. This is of paramount importance when nails are inserted without reaming to insure proper apposition with cortical bone and reproduce the natural curvature of a femur. The natural radius of curvature further enhances rotational stability of the nailed femur.

Locking of the length adjusting extension members to the base nail must result in a joint of high mechanical integrity with adequate resistance to distraction, bending, and rotational forces of the high magnitude experienced by the femur after fracture fixation. This is accomplished in the design described herein by a set of snap lock springs machined into the trailing end of each base nail. The cross section of the spring portion of the nail is a circle with two flat sides. When an extension is slid over the spring ends and pushed into the locked position, the spring arms are pushed towards each other a total of approximately 2 mm (0.080 in.). The spring force applied for this deflection is 15 pounds, for example. As the extension is slid into the locked position, a relief, machined into the extension, allows the springs to return to their original position providing rigid locking to distracting forces. The cross section of the nail and extension (a circle with flattened sides) provides rigid resistance to torsion of the nail relative to the extension. To provide enhanced operation of the spring arms when an inter-locking screw is used, the locking screw passes through the extension and between the spring arms, thereby preventing the springs from moving together and unlocking.

While the proposed system is designed for the option of a non-reamed nail, the surgeon may ream if his philosophy dictates it. Materials are not specific in the system. State of the art might indicate any suitable material such as stainless steel, titanium, titanium alloy, or composites. Furthermore, the system is not only applicable to femoral intramedullary nails, but any long bone application can be considered. Also, while it is generally desirable for a nail to be similarly curved to match its associated bone, there may be occasions when it is desirable for the nail to be straight, even when the bone is curved.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 4 is a longitudinal cross section view of an extension member which, when attached to the base nail of FIGS. 2 and 3, results in the modular nail illustrated in FIG. 1;

FIG. 7 is a detail side elevation view illustrating a part of the base nail illustrated in FIGS. 2 and 3;

FIG. 8 is a detail perspective view illustrating one end of the base nail illustrated in FIGS. 2 and 3;

FIG. 9 is a detail side elevation view showing a portion of the modular nail positioned within a bone, the bone being cut away and shown in section for purposes of clarity;

FIG. 10 is a cross section view taken generally along line 10—10 in FIG. 9;

DETAILED DESCRIPTION OF THE PREFERRED EMBODIMENT

Figure 1:
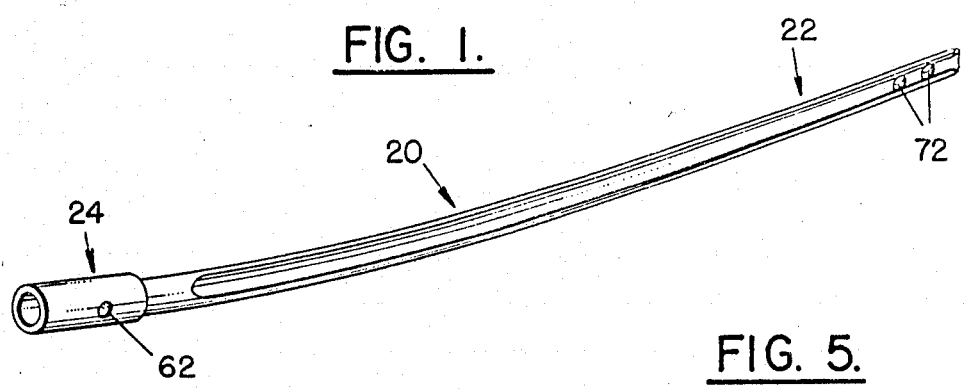
FIG. 1 is a perspective view of a modular intramedullary nail embodying the invention.
Figure 2:
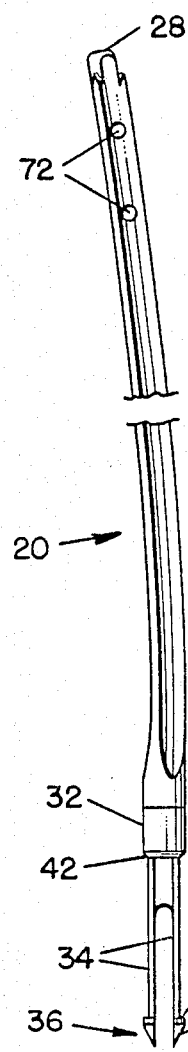
FIGS. 2 and 3 are top plan and side elevation views, respectively, of a base nail forming one component of the nail system illustrated in FIG. 1.
Figure 3:
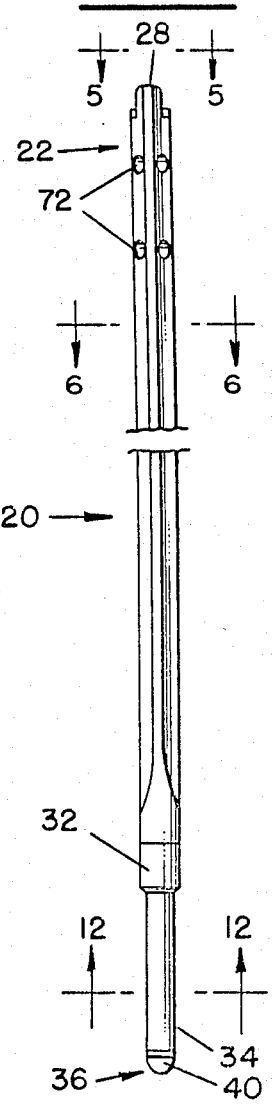

Turn now to the drawings and initially to FIG. 1 which illustrates a modular intramedullary nail 20 incorporating the features of the present invention. The nail 20 is comprised of two major components, namely an elongated base nail 22 (see FIGS. 2 and 3) and an extension member 24 (see FIG. 4) intended for selective attachment to one end of the base nail. The modular intramedullary nail 20 is intended for the repair of long bone fractures, most notably, the femur and tibia, although all other fractured long bones are candidates for receiving the nail of the present invention. In a typical femoral construction, as described and illustrated herein, the base nail 22 is preferably anatomically curved to a radius of approximately 60 to 80 inches. Many other nails which are commonly used in femoral applications are straighter, for example, curved to a radius of 100 inches, and have the undesirable effect of straightening the bone as they are inserted.

Figure 5:
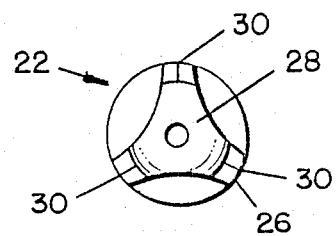
FIG. 5 is an end elevation view taken generally along line 5—5 in FIG. 3.
Figure 6:
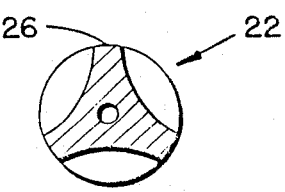
FIG. 6 is a cross section view taken generally along line 6—6 in FIG. 3.

In its mid regions, the base nail 22 has a very deeply fluted or tri-flanged cross sectional shape, each flange being represented by the numeral 26 (FIGS. 5 and 6). Most other nails currently in use are less deeply fluted and have more of a clover leaf profile. An extreme tip 28 of the base nail at its leading end is moderately blunt (FIGS. 5 and 7), displaying a radius, for example, of approximately 0.125 inches. Each of the flanges 26 terminates at a sharp point 30 at locations spaced from the tip 28. The advantages of the tri-flanged cross sectional shape of the nail are (1) that the intramedullary canal of the bone does not have to be reamed out before the nail is inserted; (2) that the blood supply is disrupted to a lesser extent; and (3) that the edges of the flanges 26 digging into the bone reduce the ability of the nail to undesirably rotate inside the bone or the individual bone fragments to rotate relative to the nail or to each other.

At a trailing end of the base nail 22, the flanges 26 are faired into a cylindrical bearing region 32. A pair of generally parallel, spaced apart, engagement tongs 34 (FIG. 8) extend away from the bearing region 32 and are resilient in directions toward and away from each other. Each of the engagement tongs terminates at an outwardly directed locking barb 36 (see especially FIGS. 2, 3 and 8) which has a locking surface 38 inboard from its extreme end which lies in a plane transverse of the longitudinal axis of the base nail 22. A cam surface 40 is tapered from the locking surface 38 down to a point at the extreme end of the barb 36. The engagement tongs have a cylindrical outer surface of reduced diameter than that of the bearing region 32 and a transverse bearing surface 42 is defined at the interface between the bearing region 32 and the engagement tongs 34. This construction is clearly seen in FIGS. 2, 3, and 4.

Turn now to FIG. 4 which most clearly illustrates the extension member 24. As seen therein, the extension member is an elongated cylinder having a longitudinal bore 44 extending between a first end 46 and a second end 48. A counterbore 50 having substantially the same diameter as the cylindrical bearing region 32 on the base nail 22 is formed adjacent the end 46. In a somewhat similar fashion, a second counterbore 52 is formed adjacent the end 48. The counterbore 50 terminates at an annular bearing surface 54 lying in a plane transverse of a longitudinal axis of the extension member 24. In like manner, the second counterbore 52 terminates at an annular locking surface 56 which also lies in a plane transverse of the longitudinal axis thereof. The counterbores 50 and 52 thereby define between them a supporting member 58 which extends to a cylindrical supporting surface 60. The inner diameter of the supporting surface 60 is substantially equal to the outer diameter of the engagement tongs 3 and the length of the supporting member 58 is substantially equal to that of the engagement tongs as they extend between the transverse bearing surface 42 and the locking surface 38.

Figure 11:
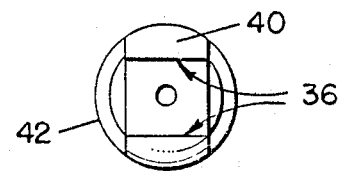
FIG. 11 is an end elevation view taken generally from the lower end of the modular nail illustrated in FIG. 3.
Figure 12:
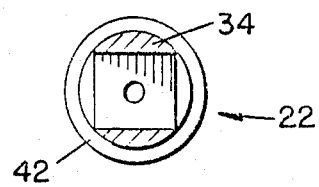
FIG. 12 is a cross section view taken generally along line 12—12 in FIG. 3.

As the end 46 of the extension member 24 is advanced toward the trailing end of the base nail 22 for intended engagement therewith, the locking barbs 36 engage the extension member 24 (see FIGS. 9 and 10). The cam surfaces 40 on the barbs specifically engage the counterbore 50 as they advance into and through the longitudinal bore 44. The engagement tongs 34 are thereby radially depressed toward one another until, with continued movement of the extension member toward the base nail, the annular bearing surface 54 comes into engagement with the transverse bearing surface 42 of the base nail. When this occurs, the locking surfaces 38 of the barbs 36 move just past the annular locking surfaces 56 within the counterbore 52. At this point, locking barbs 36 snap radially outwardly thereby causing mutual engagement of the locking surfaces 56 and 38. When this occurs, the bearing region 32 is intimately received within the counterbore 50 and the supporting surface 6 is intimately received on the outer surfaces of the engagement tongs thereby preventing inadvertent separation of the base nail and the extension member (see FIGS. 10, 11, and 12). By reason of the construction disclosed, the strength of the resultant modular nail 20 is also maximized.

The strength of the resultant modular nail 20 can be even further enhanced by forming the mutually engaging region 32 and counterbore 50 so as to have a locking taper. By reason of this construction, the strength of the nail 20 at the interface between the base nail 22 and the extension member 24 is further increased and relative motion between the base nail and the extension member substantially eliminated.

While not always necessary, it is often times desirable to positively affix the modular nail 20 to the fractured bone to prevent its longitudinal movement relative to the bone and, even more properly, to prevent relative motion between the nail and the bone. Thus, as seen in FIG. 4, a transverse bore 62 is formed in the extension member 24. Then, with the modular nail 20 already positioned within the intramedullary canal 66 of a long bone 68 (FIG. 9), a suitable screw 70 pierces the bone and extends through the transverse bore 62 and between the engagement tongs 34 as they are received within the longitudinal bore 44. The outermost surfaces of the shank of the screw 70 prevent the engagement tongs 34 from moving radially towards one another and thereby unlocking from engagement with the extension member, thereby further assuring the integrity of the modular nail 20. To supplement the benefit obtained from the screw 70, a similar screw or screws may be utilized at the leading end of the base nail, passing transversely through the bone and through the holes 7 at the leading end of the base nail.

The construction just described provides a modular system whereby several base nails of different lengths and several extension members of different lengths can be selected in various combinations such that virtually any length of nail as an end product can be constructed in the operating room at the time of surgery. Furthermore, by turning the extension member 180°, a left nail becomes a right nail, and visa versa. Additionally, the surgeon may adjust the length of the resultant nail by removing and changing the extension member while leaving the base nail in position within the bone. For removal of the extension member, an appropriate tool may be inserted into the open end of the extension member so as to engage the cam surfaces 40 of the locking barbs 36, thereby squeezing the engagement tongs 34 together until the locking surfaces 38 are no longer constrained by the locking surfaces 56. This concept of modularity is a particularly desirable feature of the present invention. It is customary for present intramedullary femoral nail systems to require up to 84 different nails to fit a wide range of patient sizes in both "lefts" and "rights". In contrast, a system utilizing the concept of the present invention, would only require about 18 pieces to cover the same range of sizes in both "lefts" and "rights".

Materials used for fabrication of the base nail and of the extension member may be stainless steel, titanium, titanium alloy, or composites. The material used for the base nail may be the same as that use for the extension member, or the material used for the one may be different from that used for the other except that it is not desirable to use a titanium or titanium alloy component with a stainless steel component. This latter limitation is due to the occurrence of galvanic coupling which would thereby adversely occur in the fluid environment of the body.

While a preferred embodiment of the invention has been disclosed in detail, it should be understood by those skilled in the art that various other modifications may be made to the illustrated embodiment without departing from the scope of the invention as described in the specification and defined in the appended claims.

What is claimed is:

1. A modular intramedullary nail for the repair of long bone fractures comprising:
    an elongated base nail having a longitudinal axis and generally conforming to the shape of the bone, said base nail extending between a leading end and a trailing end, said base nail having a cylindrical bearing region adjacent said trailing end, a pair of generally parallel, spaced apart engagement tongs extending away from said bearing region and being resilient in directions toward and away from each other, each of said engagement tongs terminating at an outwardly directed locking barb tapered from a locking surface lying in a plane transverse of the longitudinal axis to a point at the extreme end thereof, said engagement tongs having a cylindrical outer surface of reduced diameter from that of said bearing region, a transverse bearing surface defined at the interface between said bearing region and said engagement tongs; and
    an extension member intended for selective attachment to said trailing end of said base nail, said extension member having a longitudinal axis and a longitudinal bore therethrough and extending between a first end and a second end, said first end having a first counterbore therein terminating at an annular bearing surface lying in a plane transverse of the longitudinal axis, said second end having a second counterbore therein terminating at an annular locking surface lying in a plane transverse of the longitudinal axis, the first and second counterbores defining therebetween a supporting member with a cylindrical supporting surface, the inner diameter of the first counterbore being substantially equal to the outer diameter of said bearing region, the inner diameter of said supporting surface being substantially equal to the outer diameter of said engagement tongs, the length of said supporting member being substantially equal to that of said engagement tongs excluding said locking barbs;
    whereby, as said first end of said extension member is advanced toward and into engagement with said trailing end of said base nail, said locking barbs slidably engage said extension member as they advance into and through the longitudinal bore thereof, and said engagement tongs are radially depressed towards one another until, with continued movement of said extension member toward said base nail, said bearing surface of said extension member engages said bearing surface of said base nail, whereupon said locking barbs snap radially outwardly such that said locking surfaces thereon engage said locking surface on said extension member, said bearing region being intimately received in the first counterbore and said supporting surface being intimately received on said outer surfaces of said engagement tongs thereby preventing inadvertent separation of said base nail and said extension member and maximizing strength of said modular nail.

2. A modular intramedullary nail as set forth in claim 1 wherein said base nail has a plurality of peripherally spaced, radially directed, longitudinal flanges extending from a location spaced from said leading end to said bearing region.

3. A modular intramedullary nail as set forth in claim 1 wherein said extension member has a transverse bore therethrough; and including:
a cross screw received through the transverse bore and through the space between said engagement tongs and engaged with the fractured bone for preventing relative motion of said modular nail and the fractured bone.

4. A modular intramedullary nail as set forth in claim 2 wherein said base nail has a rounded tip at said leading end; and wherein there are three of said longitudinal flanges, each terminating at a sharp point adjacent said leading end.

5. A modular intramedullary nail as set forth in claim 1 wherein said base nail and said extension member are each composed of any one of titanium or titanium alloy or of composite materials.

6. A modular intramedullary nail as set forth in claim 1 wherein said base nail and said extension member are each composed of any one of stainless steel or of composite materials.

7. A modular intramedullary nail as set forth in claim 1 wherein said bearing region on said base nail and said first counterbore in said extension member are similarly formed with a locking taper.

8. A system of providing a modular intramedullary nail of proper sizing for a particular patient comprising:
an inventory of at least a pair of elongated base nails of different lengths, each adapted to be completely imbedded in the bone and having a longitudinal axis and generally conforming to the shape of the bone, said base nail extending between a leading end and a trailing end, each including cylindrical support means at said trailing end thereof;
an inventory of at least a pair of extension members of different lengths, each adapted to be completely imbedded in the bone and having a longitudinal axis and a longitudinal bore therethrough intended to be joined with said base nail by intimate reception of said cylindrical support means into the bore; and
first locking means at said trailing end of each of said base nails for reception within the longitudinal bore of a selected one of said extension members and second locking means on each of said extension members engageable with said first locking means upon relative movement of said base nail toward said extension member to a fully locked position whereat said base nail and said extension member become a rigid unit and are positively prevented from unintended separation while enabling relative rotational positioning of said extension member and said base nail for fixedly attaching a selected one of said extension members to a selected one of said base nails to thereby obtain the proper size of intramedullary nail intended for fixation to and completely imbedded in the bone of the particular patient during the healing process.

9. A system as set forth in claim 8 wherein said base nail has a plurality of peripherally spaced, radially directed, longitudinal flanges extending from a location spaced from said leading end to said bearing region.

10. A system as set forth in claim 8 wherein each of said extension members has a transverse bore therethrough; and including:
a cross screw received through the transverse bore and through said locking means and engaged with the fractured bone for preventing relative motion of said modular nail and the fractured bone.

11. A system as set forth in claim 8 wherein said base nail and said extension member are each composed of any one of titanium or titanium alloy or of composite materials.

12. A system as set forth in claim 8 wherein said base nail and said extension member are each composed of any one of the stainless steel or of composite materials.

13. A system as set forth in claim 8 wherein said mutually cooperating support means on said base nail and the bore on said extension member include mutually engaging surfaces which are similarly formed with a locking taper.

14. A modular intramedullary nail for the repair of long bone fractures comprising:
an elongated base nail adapted to be completely imbedded in the bone and having a longitudinal axis and generally conforming to the shape of the bone, said base nail extending between a leading end and a trailing end, said base nail including cylindrical support means adjacent said trailing end thereof;
an extension member adapted to be completely imbedded in the bone and having a longitudinal axis and a longitudinal bore therethrough, and extending between a first end and a second end, said extension member intended for selective attachment to said trailing end of said base nail by intimate reception of said cylindrical support means into the bore thereof; and
first locking means at said trailing end of said base nail for reception within the longitudinal bore of a selected one of said extension members and second locking means on said extension member engageable with said first locking means upon relative movement of said base nail toward said extension member to a fully locket position whereat said base nail and said extension member become a rigid unit and are positively prevented from unintended separation while completely imbedded in the bone during the healing process, said first and second locking means fixedly attaching said extension member to an associated one of said base nails to prevent inadvertent separation of said base nail and said extension member while enabling relative rotational positioning of said extension member and said base nail and while maximizing strength of said modular nail.

15. A modular intramedullary nail as set forth in claim 14 wherein said first locking means includes:

a pair of generally parallel, spaced apart engagement tongs extending away from said cylindrical support means and integral with said base nail, said tongs being resilient in directions toward and way from each other, each of said engagement tongs terminating at an outwardly directed locking barb tapered from a locking surface lying in a plane transverse of the longitudinal axis of said base nail to a point at the extreme end thereof, said engagement tongs having a cylindrical outer surface of reduced diameter from that of said support means, a transverse bearing surface defined at the interface between said support means and said engagement tongs; and wherein said first end of said extension member having a first counterbore therein terminates at an annular bearing surface, said second end having a second counterbore therein terminating at an annular locking surface lying in a plane transverse of the longitudinal axis thereof, said second locking means including said annular locking surface, the first and second counterbores defining therebetween a supporting member with a cylindrical supporting surface, the inner diameter of the first counterbore being substantially equal to the outer diameter of said cylindrical support means, the inner diameter of said supporting surface being substantially equal to the outer diameter of said engagement tongs, the length of said supporting member being substantially equal to that of said engagement tongs excluding said locking barbs;

whereby, as said first end of said extension member is advanced toward and into engagement with said trailing end of said base nail, said locking barbs slidably engage said extension member as they advance into and through the longitudinal bore thereof, and said engagement tongs are radially depressed toward one another until, with continued movement of said extension member toward said base nail, said bearing surface of said extension member engages said bearing surface of said base nail, whereupon said locking barbs snap locking surfaces thereon engage said locking surface on said extension member, said cylindrical support means being intimately received in the first counterbore and said supporting surface being intimately received on said outer surfaces of said engagement tongs thereby preventing inadvertent separation of said base nail said extension member and maximizing strength of said modular nail.

16. A modular intramedullary nail as set forth in claim 15 wherein said base nail has a plurality of peripherally spaced, radially directed, longitudinal flanges extending from a location spaced from said leading end to said bearing region.

17. A modular intramedullary nail assembly as set forth in claim 15 wherein said extension member has a transverse bore therethrough; and including:

a cross screw received through the transverse bore and through the space between said engagement tongs and engaged with the fractured bone for preventing relative motion of said modular nail and the fractured bone.

18. A modular intramedullary nail as set forth in claim 16 wherein said base nail has a rounded tip at said leading end; and wherein there are three of said longitudinal flanges, each terminating at a sharp point adjacent said leading end.

19. A modular intramedullary nail as set forth in claim 14 wherein said base nail and said extension member are each composed of any one of titanium or titanium alloy or of composite materials.

20. A modular intramedullary nail as set forth in claim 14 wherein said base nail and said extension member are each composed of any one of stainless steel or of composite materials.

21. A modular intramedullary nail as set forth in claim 15 wherein said bearing region on said base nail and said first counterbore in said extension member are similarly formed with a locking taper.

* * * * *